United States Patent
Rosson et al.

(10) Patent No.: US 8,890,077 B2
(45) Date of Patent: Nov. 18, 2014

(54) REMOTE DETECTION OF RADIATION

(75) Inventors: Robert L. Rosson, Atlanta, GA (US); Bernd Kahn, Atlanta, GA (US); Brent Wagner, Marietta, GA (US); David Roberts, Smyrna, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 28 days.

(21) Appl. No.: 13/383,463

(22) PCT Filed: Aug. 4, 2010

(86) PCT No.: PCT/US2010/044369
§ 371 (c)(1), (2), (4) Date: Jan. 11, 2012

(87) PCT Pub. No.: WO2011/017410
PCT Pub. Date: Feb. 10, 2011

(65) Prior Publication Data
US 2012/0112076 A1 May 10, 2012

Related U.S. Application Data

(60) Provisional application No. 61/231,129, filed on Aug. 4, 2009.

(51) Int. Cl.
*G01T 1/205* (2006.01)
(Continued)

(52) U.S. Cl.
CPC .............. *G01T 7/00* (2013.01); *G01N 21/6402* (2013.01); *G01S 17/88* (2013.01);
(Continued)

(58) Field of Classification Search
CPC . G01N 27/622; G01N 21/6404; G01N 21/78; G01N 2030/77; G01N 2033/0093; G01N 2021/7786; G01N 2021/392

USPC ........... 250/361 R, 458.1, 459.1, 461.1, 362, 250/368, 390.11, 370.02
See application file for complete search history.

(56) References Cited

U.S. PATENT DOCUMENTS 3,768,908 A 10/1973 Zaromb
6,281,502 B1 * 8/2001 Pineau et al. ............. 250/361 R
(Continued)

OTHER PUBLICATIONS

Garner et al., Molecular Nitrogen Fluorescence Lider for Remote Sensing of The Auroral Ionosphere, 1994, Phippips Laboratory, 94 5 23 102, 1-34.*

(Continued)

*Primary Examiner* — David Porta
*Assistant Examiner* — Djura Malevic
(74) *Attorney, Agent, or Firm* — Troutman Sanders LLP; Ryan A. Schneider; Troy S. Kleckley

(57) ABSTRACT

Various embodiments of the present invention provide a method of detecting inaccessible radiation sources by measuring corresponding ions and excited molecules created by radiation, using LIDAR technology. The LIDAR system of the present invention employs a pulsed laser transmitter, a telescope receiver, and associated control and acquisition systems. Light propagates out from the laser transmitted and is directed into the volume surrounding the radioactive source, or the "ion cloud." The ion cloud absorbs the transmitted light, which induces the non-fluorescing ions to fluoresce. Light from the ion cloud is then backscattered and the telescope receiver subsequently collects the photons from the backscattered light. The intensity of the fluorescence (determined by the photon count) is measured, which provides an indication of the number density of the ionized atoms. Algorithms can then be used to relate the measured ionization rates to the source activity.

17 Claims, 4 Drawing Sheets

(51) Int. Cl.
*G01T 7/00* (2006.01)
*G01N 21/64* (2006.01)
*G01S 17/88* (2006.01)
*G01N 21/17* (2006.01)
*G01N 21/47* (2006.01)
*G01S 17/95* (2006.01)

(52) U.S. Cl.
CPC .......... *G01N 2021/1793* (2013.01); *G01N 2021/4709* (2013.01); *G01N 2021/6419* (2013.01); *G01S 17/95* (2013.01)
USPC .......... 250/361 R; 250/458.1; 250/459.1; 250/461.1; 250/368; 250/390.11; 250/370.02

(56) References Cited

U.S. PATENT DOCUMENTS

2006/0231771 A1    10/2006  Lee et al.
2008/0149838 A1     6/2008  Parvin
2010/0308225 A1*   12/2010  Nakamura ............... 250/361 R

OTHER PUBLICATIONS

International Search Report and Written Opinion dated Oct. 20, 2010 for related PCT Patent Application No. PCT/US2010/044369.

* cited by examiner

REMOTE DETECTION OF RADIATION

CROSS-REFERENCE TO RELATED APPLICATIONS

The present application claims the benefit of International Patent Application Serial Number PCT/US2010/044369, filed 4 Aug. 2010, which claims the benefit of U.S. Provisional Patent Application Ser. No. 61/231,129, filed 4 Aug. 2009, all of which are hereby incorporated by reference in their entirety as if fully set forth below.

BACKGROUND OF THE INVENTION

1. Field of the Invention

The various embodiments of the present invention relate generally to detecting radioactive materials, and more specifically to the indirect detection of radioactive material by directly measuring the ionized and excited molecules within proximity of the radioactive material.

2. Description of Related Art

Radioactivity occurs when an atom has extra energy and desires to release this energy to become more stable. This spontaneous release of energy is called radioactive decay. When the nucleus of a radionuclide spontaneously gives up its extra energy, it does so by emitting alpha particles, beta particles, or gamma rays.

Radioactivity is a natural phenomena of nature, however, high levels of radioactivity present many health concerns as alpha particles, beta particles, and gamma rays, if absorbed by the human body, can cause grave cellular damage. Such health concerns can be mitigated or entirely avoided if dangerous levels of radiation can be easily detected and identified.

Many of the current techniques used to indirectly detect radioactivity involve the passive detection of ultraviolet (UV) light created by the effect of radiation on the surrounding atmosphere. This technique, however, cannot be used to detect radiation during daylight due to the large background interference of solar UV light. Other techniques require close proximity to the radioactive source, which, as stated above, presents various health concerns. This is especially true for nuclear materials that emit short range alpha particles, because the radiation only travels a few centimeters (cm) in air.

Accordingly, there is a need for a technique that enables detection of dangerous levels of radioactivity during daylight at a distance. It is to this need that the present invention is directed.

BRIEF SUMMARY OF THE INVENTION

Briefly described, in preferred form, the present invention provides a method of indirectly measuring radioactivity by actively and directly measuring ionization levels in the proximity of radioactive source, and correlating such ionization levels to a radioactivity measurement.

Accordingly, in an exemplary embodiment of the present invention, a method of indirectly detecting a radioactive source by measuring ionization proximate the radioactive source comprises transmitting pulsed light proximate the radioactive source, inducing non-fluorescing ions proximate the radioactive source to become fluorescing ions with the pulsed light, and receiving backscattered light emitted from proximate the radioactive source, wherein the backscatter light includes photons emitted from the fluorescing ions.

Various other exemplary embodiments of the present invention provide a method of indirectly detecting a radioactive source at a distance by measuring ionization proximate the radioactive source comprising transmitting pulsed light into a volume surrounding the radioactive source, wherein the volume comprises both fluorescing and non-fluorescing ions, inducing the non-fluorescing ions with the pulsed light causing the non-fluorescing ions to become fluorescing ions, and receiving backscattered light emitted from the volume surrounding the radioactive source, wherein the backscatter light includes photons emitted from the fluorescing ions as well as photons from the pulsed light.

The methods can further comprise measuring an intensity of the backscattered light by detecting the number of photons in the backscattered light.

The methods can further comprise correlating the intensity of the backscattered light to a corresponding radioactivity measurement.

The fluorescing and non-fluorescing ions can be, for example, nitrogen, oxygen, argon, or helium ions.

The transmitted pulsed light can comprise a transmitted light of a wavelength that causes the non-fluorescing ions to fluoresce.

Another exemplary embodiment of the present invention provides a method of indirectly detecting an inaccessible radioactive source at a distance by measuring ionization proximate the radioactive source comprising exciting an atomic or molecular species of interest to an excited state, wherein the molecular species of interest subsequently decays to a lower energy state by emitting photons with a longer wavelength, and receiving the photons emitted by the molecular species of interest.

The method can further comprise measuring an intensity of the photons.

The method can further comprise correlating the intensity of the photons to a corresponding radioactivity measurement.

The molecular species of interest can be molecular nitrogen, molecular oxygen, argon, or helium.

Other exemplary embodiments of the present invention provide an apparatus used to detect inaccessible radiation sources at a distance by measuring corresponding ions created by radiation comprising at least one pulsed laser transmitter adapted to transmit light into a volume surrounding a radioactive source; a telescope receiver adapted to receive backscattered light, and an electronic system that measures the time of flight between an emission of the laser pulse and a detection of the backscattered light to enable a range to an ion cloud produced by the radioactive source.

The apparatus can further comprise a photodetector adapted to convert the backscattered light into an electronic signal.

The apparatus can further comprise a narrowband filter adapted to filter noise that interferes with the backscattered light.

DETAILED DESCRIPTION OF THE INVENTION

Figure 1:
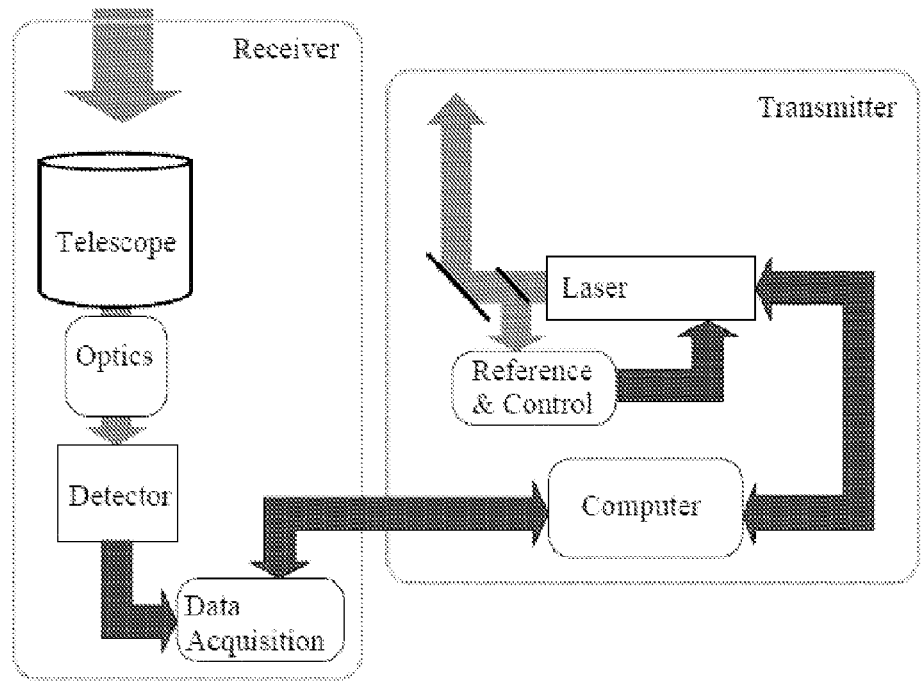
FIG. 1 provides an illustration of a LIDAR process in accordance with an aspect of the present invention.

Various embodiments of the present invention provide a method of detecting radiation sources by measuring corresponding ions and excited molecules created by radiation. Although preferred embodiments of the invention are explained in detail, it is to be understood that other embodiments are contemplated. Accordingly, it is not intended that the invention be limited in its scope to the details of construction and arrangement of components set forth in the following description or illustrated in the drawings. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural references unless the context clearly dictates otherwise. Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those Radioactive sources emit various forms of radiation such as alpha particles, beta particles, and gamma rays which excite or ionize molecules in the surrounding air, creating "ion clouds", i.e. These various forms of radiation have unique penetration depths, with alpha particles ranging to a few centimeters in air, beta particles ranging to about a meter in air, and gamma rays ranging to many meters in air. Because alpha particles have such a small penetration depth, they are difficult to detect as they can be blocked by materials as thin as a piece of paper. Beta particles and gamma rays have greater penetration depths than alpha particles, and are therefore more accessible. Alpha particles, however, have stronger ionization rates than beta particles and gamma rays. Because a radioactive source can be encased in a variety of materials, therefore potentially blocking specific forms of radiation, specifically alpha particles, it is desirable to have a method designed to detect all forms of radiation.

Embodiments of the present invention utilize technology that actively detects and measures both excited and ionized molecules in proximity to the radioactive source (i.e., within the "ion cloud"). Because the excitation and ionization of molecules is dependent on radioactivity, the measurements of such molecules can then be correlated to a radioactivity level, therefore enabling the identification of harmful radioactivity levels. Measuring the ionization of molecules is preferable over measuring molecules in an excited state because ions have a significantly longer lifetime than excited states, and are therefore more likely to leak out of an enclosure and be detected.

Nitrogen comprises approximately 78% of air and is responsible for much of the auroral emissions in the UV, which are primarily due to excited and/or ionized nitrogen molecules caused by cosmic radiation. Because of nitrogen's prevalence in air, its ionization, caused by alpha and beta particles, and gamma rays, is more plentiful than the smaller components in air, such as oxygen and helium. Ionized nitrogen, however, can be difficult to detect because only 0.5% of the nitrogen ions generated by radiation create light naturally. Stated another way, 200× more nitrogen ions are generated than are naturally fluorescing. It is important to understand that nitrogen, as well as other components in air, are excited and ionized naturally because of UV radiation. Therefore, the presence of excited and/or ionized nitrogen does not necessarily indicate dangerous radioactivity. High levels of excited or ionized nitrogen, however, provides an indication of dangerous radioactivity.

It is therefore an object of the present invention to provide a system for actively detecting and measuring the excitation and ionization of molecules in proximity with a radioactive source and correlating such measurement to a radioactivity level. The embodiments of the present invention can be attuned to specific molecules, such as nitrogen, oxygen, and helium.

More specifically, the various embodiments of the present invention provide a system of indirectly detecting radioactivity by measuring escaping ionized air created by the radioactivity using Light Detection and Ranging (LIDAR) technology. This systems enables the remote detection (i.e., from a distance) of inaccessible radiation sources ranging from 1-1000 meters (m) away during both daylight and nighttime.

LIDAR technology is an optical remote sensing technology that measures properties of scattered light in air. LIDAR technology can be utilized to measure ionization resulting from alpha and beta particles and gamma rays from a distance. The LIDAR system of the present invention employs a pulsed laser transmitter, a telescope receiver, and associated control and acquisition systems. Pulsed light propagates out from the laser transmitter and is directed into the volume surrounding the radioactive source, or the "ion cloud." The ion cloud absorbs the transmitted light. This absorption induces otherwise undetectable, non-fluorescing ions to fluoresce. Light from the ion cloud is then backscattered and the telescope receiver subsequently collects the photons from the backscattered light. The intensity of the fluorescence (determined by the photon count) is measured, which provides an indication of the number density of the ionized atoms. FIG. 1 provides an illustration of this process in accordance with an aspect of the present invention.

Figure 2:
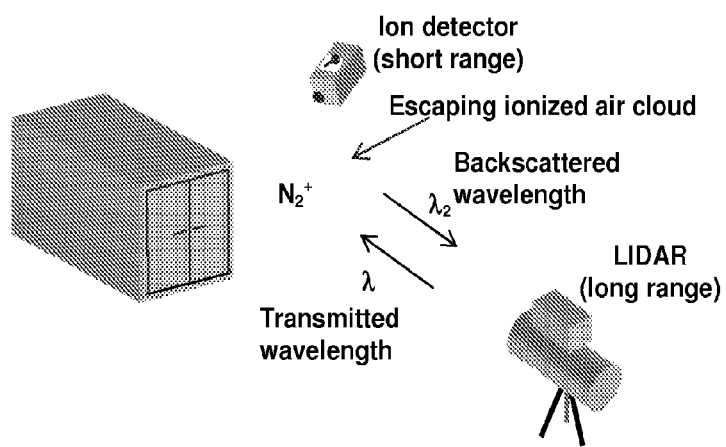
FIG. 2 provides an illustration of a LIDAR system in accordance with an aspect of the present invention FIG. 3 provides a graphical representation of a nitrogen emission spectrum.

The LIDAR system of the present invention, illustrated in FIG. 2, can operate at various frequencies and wavelengths. Specifically, the light emitted from the laser can be pulsed at various frequencies and wavelengths. The pulsed nature enables ranging information to be collected and reduces the effects of background interference. For optimum performance, the LIDAR system of the present invention can be attuned to the specific parameters of the molecular ionization to be measured. Using nitrogen as an example, only 0.5% of the ions generated by radiation create light naturally. If the non-fluorescing ions remain in such a state, 95.5% of nitrogen ions will go undetected, therefore inhibiting the accurate measurement of ionization. The LIDAR system of the present invention can be customized such that the pulsed light emitted from the laser is of a sufficient frequency and wavelength to induce non-fluorescing nitrogen ions to fluoresce, therefore enabling more sensitive ionization detection. Similarly, the LIDAR system of the present invention can be attuned to other molecular ionizations, such as oxygen, argon, and helium ionization.

Figure 3:
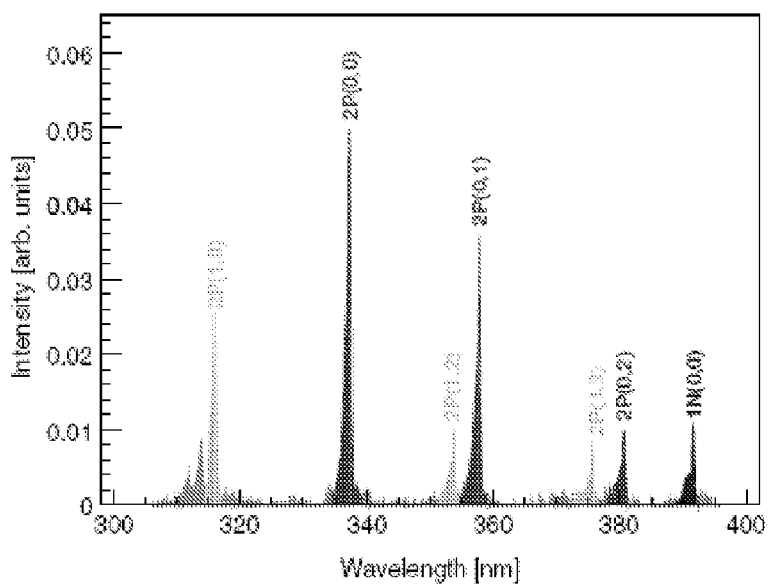
Figure 4:
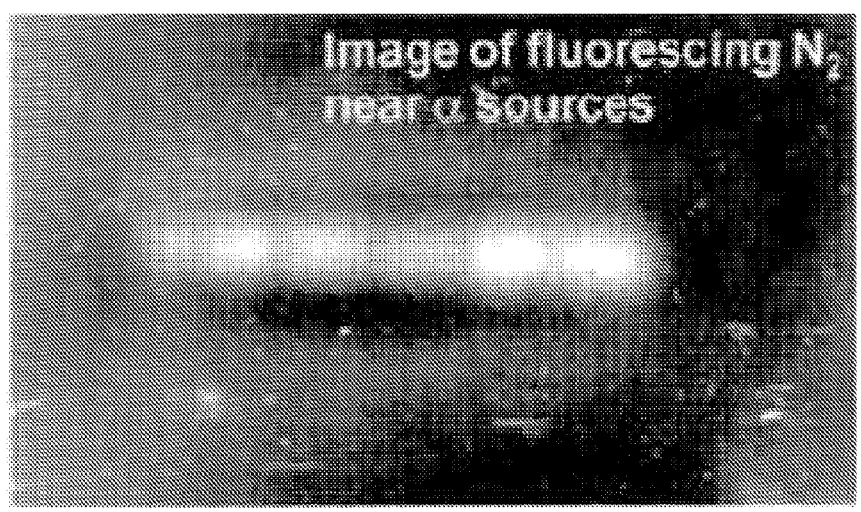
FIG. 4 provides an image of fluorescing nitrogen ions near alpha radiation sources.
Figure 5:
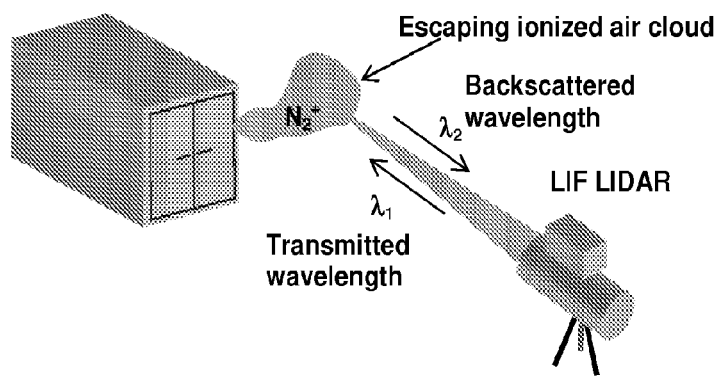
FIG. 5 provides an illustration of a LIF LIDAR system in accordance with an aspect of the present invention FIGS. 6 and 7 provide graphical representations of absorption transitions for molecular nitrogen.

The spectroscopy of the molecule to be measured influences the specific tuning of the LIDAR system. For example, the LIDAR system can be tuned to detect molecular nitrogen ionization using molecular nitrogen spectroscopy data. For illustrative purposes, FIG. 3 provides a graphical representation of a nitrogen emission spectrum, and FIG. 4 provides a UV image of fluorescing nitrogen ions near alpha radiation sources. As shown in the graph in FIG. 3, the intensity of emitted light is dependent on wavelength. Therefore, an embodiment of the present invention provides a LIDAR system wherein the laser transmitted light wavelength is sufficient in inducing the non-fluorescing nitrogen ions to fluoresce after absorption.

The preferred wavelength for the laser light is slightly temperature dependent and varies between 390.5 nanometers (nm) and 391.5 nanometers. After absorption by the ions in the "ion cloud," a small portion of the light is then "backscattered" back towards the LIDAR system and received by the LIDAR receiver telescope. The backscattered light can have the same wavelength as the transmitted pulse, referred to as "elastic scattering," or a different wavelength, referred to as "inelastic scattering." The inelastically-scattered light can be used to detect the ions. The inelastically scattered light produced by the fluorescing atoms can be received by the LIDAR receiver telescope.

The LIDAR receiver telescope can further comprise a photodetector, which converts the collected light into an electronic signal. To reduce noise resulting from solar and artificial illumination, the LIDAR system of the present invention can comprise a narrowband filter, which precedes the photodetector, and is adapted to block extraneous light that may interfere with accurate photon detection. This filtering enables longer distance detection and daylight operation.

Figure 6:
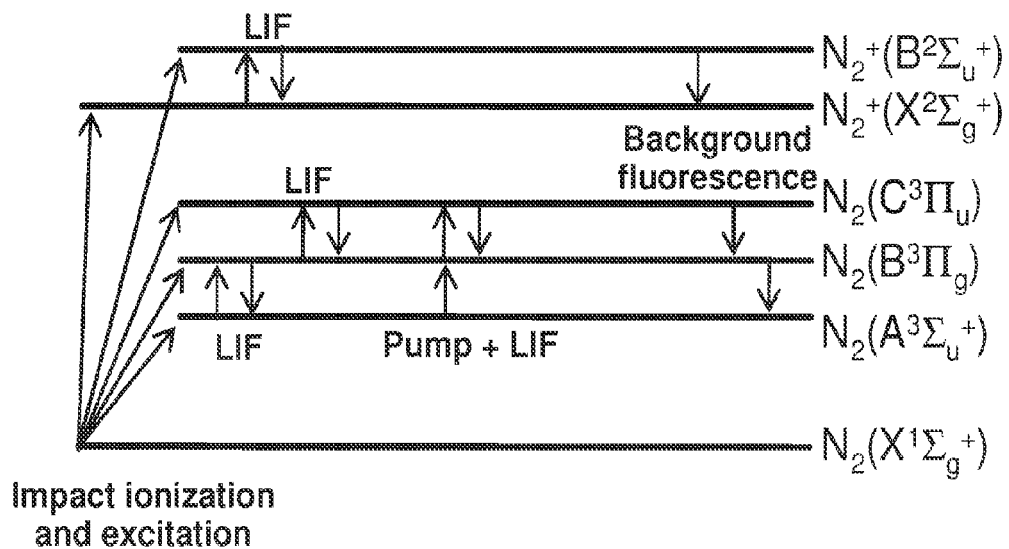
Figure 7:
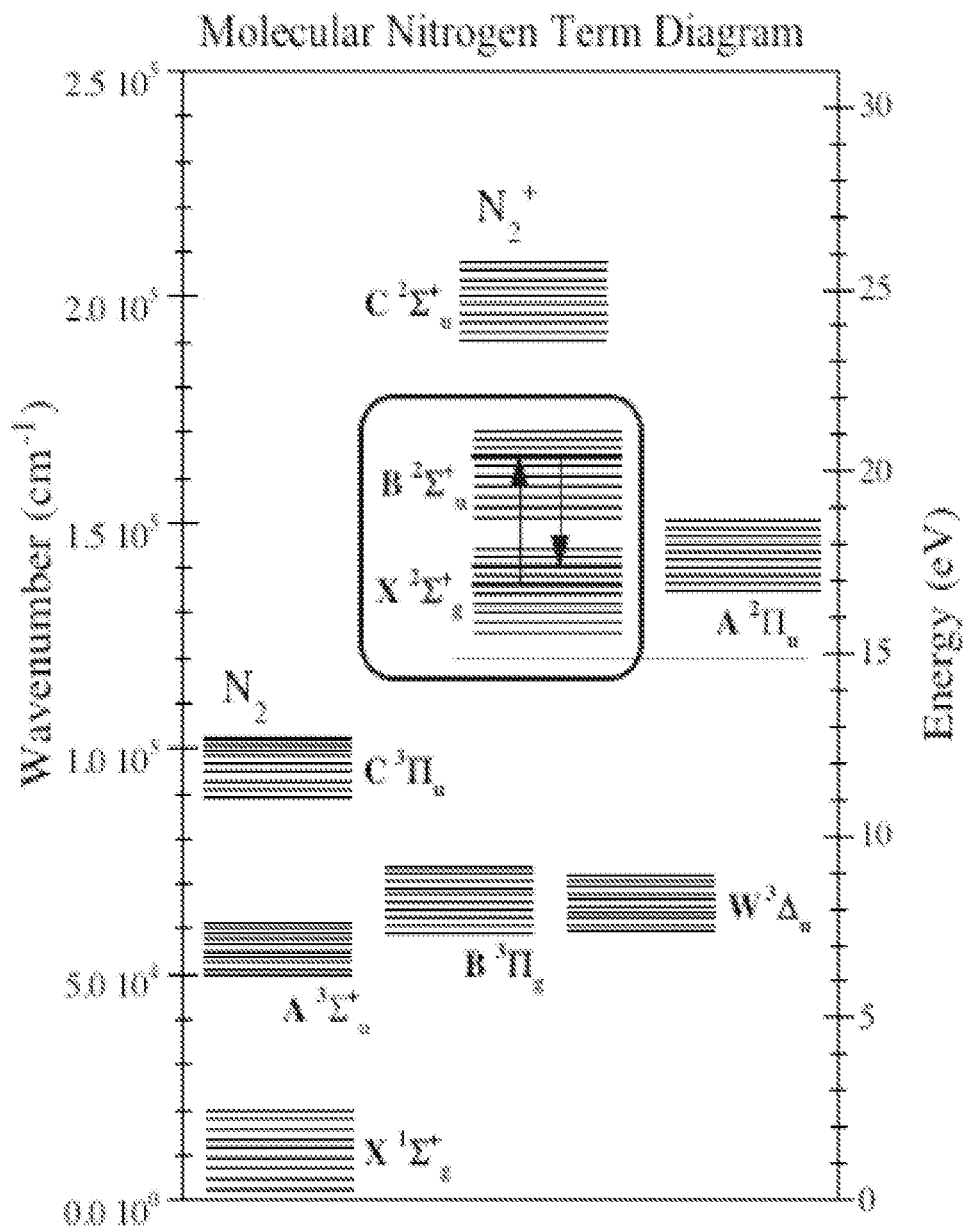

More specifically speaking, in this LIF LIDAR embodiment, the transmitted laser pulse excites the molecular species of interest to an excited state that subsequently decays to a lower energy state by emitting a photon with a longer wavelength. As in the general LIDAR embodiment, the magnitude of the wavelength received by telescope receiver is proportional to the number density of molecules present, which can be subsequently correlated to radioactivity. In the specific case of nitrogen, both excited and ionic nitrogen states have fluorescent transitions that can be pumped by the laser transmitter. These transitions are resonant, which drastically increase their effective backscatter cross sections at the laser wavelength and enhance the detectability of the excited and ionic states relative to the unexcited molecules. There are many absorption transitions that can be incorporated in the various embodiments of the present invention for molecular nitrogen, including: (1) $N_2(A^3\Sigma_u^+)\rightarrow N_2(B^3\Pi_g)$ between two excited states at 888.3 nm; (2) $N_2^+(X^2\Sigma_g^+)\rightarrow N_2^+(B^3\Pi_u^+)$ between two ionized states near 392.2 nm; and (3) a three-level scheme, $N_2(A^3\Sigma_u^+)\rightarrow N_2(B^3\Pi_g)\rightarrow N_2(C^3\Pi_u)$ that is pumped at 1046.9 nm for the first transition, and then probed at 337 nm using a transition between the second and third states. These absorption transitions are graphically illustrated in FIGS. 6 and 7.

The $N_2$ AB LIDAR system (absorption transition state 1) comprises one laser and excites nitrogen molecules in a single-step, $N_2[A^3\Sigma_g^+(v=v_1)]\rightarrow N2[B^3\Pi_g \ (v=v_1)]$. Subsequent decay and emission of the nitrogen molecules occur in either a single-step process, $N_2[B^3\Pi_g(v=v_2)]\rightarrow N_2[A^3\Sigma_g^+(v=v_3)]$ with emission wavelength $\lambda_2$, or a triple-step process, $N_2[B^3\Pi_g(v=v_2)]\rightarrow N_2[W^3(v=v_3)]\rightarrow N_2[B^3\Pi_g(v=v_4)]\rightarrow [A^3\Sigma_u^+(v=v_5)]$ with emission wavelengths $\lambda_2$, $\lambda_3$, and $\lambda_4$, respectively. The $N_2^+$XB LIDAR system (absorption transition state 2) also comprises one laser and excites nitrogen ions in a single step $N_2^+[X^2\Sigma_g^+(v=v_2)]\rightarrow N_2^+[B^3\Pi_u^+(v=v_2)]$. The decay and remission occur in a single step process, $N_2^+[B^3\Pi_u^+(v=v_2)]\rightarrow N_2^+[X^2\Sigma_g^+(v=v_3)]$. The $N_2$ ABC LIDAR system (absorption transition state 3) comprises two lasers. The first transition $A^3\Sigma_u^+\rightarrow B^3\Pi_g$ is optically pumped, and the subsequent excitation and decay between the $B^3\Pi_g$ and $C^3\Pi_u$ are probed. The $N_2$ ABC LIDAR system allows for higher resolution. Each system comprises its own relative backscatter cross sections to be received by the receiver, and the parameters for each system are provided in Tables 1, 2, and 3.

TABLE 1

| LIDAR | $N_2$AB | $N_2^+$XB | $N_2$ABC |
|---|---|---|---|
| $\lambda_1$(nm) | 888.3 | 391.2 | 1046.9 |
| $\lambda_2$(nm) | 888.3 | 391.2 | 337 |
| $\lambda_3$(nm) | | | 337 |
| $v_1$ | 0 | 0 | 0 |
| $v_2$ | 1 | 0 | 0 |
| $v_3$ | 0 | 0 | 0 |
| $v_4$ | | | 0 |
| $A_1$ | $7.70 \times 10^4$ | $1.14 \times 10^7$ | $5.08 \times 10^4$ |
| $A_2$ | | | $1.31 \times 10^7$ |
| $\gamma_2$ | 0.71 | 0.71 | 0.49 |

TABLE 2

| | LIDAR | | | | | |
|---|---|---|---|---|---|---|
| | $N_2$ AB | | | $N_2^+$ XB | | |
| T(K) | 200 | 500 | 1000 | 200 | 500 | 1000 |
| $J_1$ | 6 | 11 | 15 | 6 | 9 | 13 |
| $J_2$ | 7 | 12 | 16 | 7 | 10 | 14 |
| $J_3$ | 7 | 12 | 16 | 8 | 11 | 15 |
| $R(\Lambda_1, v_1, J_1)$ | 8.7% | 5.5% | 3.9% | 10.0% | 6.3% | 4.5% |
| $\lambda_1$ (nm) | 886.00 | 883.58 | 881.19 | 390.60 | 390.30 | 389.84 |
| $\lambda_2$ (nm) | 887.59 | 886.30 | 884.80 | 391.49 | 391.54 | 391.54 |
| $h_2$ | 0.50 | 0.50 | 0.50 | 0.52 | 0.52 | 0.52 |
| $T_1, T_2$ | 0.96 | 0.99 | 0.99 | 0.67 | 0.67 | 0.67 |
| $\sigma_{eff1}$ ($\times 10^{-18}$ m$^2$) | 4.0 | 2.4 | 1.7 | 51 | 31 | 21 |

TABLE 3

| | $N_2$ ABC | | |
|---|---|---|---|
| T(K) | 200 | 500 | 1000 |
| $J_1$ | 6 | 11 | 15 |
| $J_2$ | 7 | 12 | 16 |
| $J_3$ | 8 | 13 | 17 |
| $J_4$ | 9 | 14 | 18 |
| $R(\Lambda_1, v_1, J_1)$ | 8.7% | 5.5% | 3.9% |
| $\lambda_1$ (nm) | 1048.2 | 1048.18 | 1047.44 |
| $\lambda_2$ (nm) | 336.58 | 336.17 | 1047.44 |
| $\lambda_3$ (nm) | 337.21 | 337.16 | 337.05 |
| $h_3$ | 0.52 | 0.52 | 0.51 |
| $T_1$ | 0.99 | 0.99 | 0.99 |

TABLE 3-continued

| N₂ ABC | | | |
|---|---|---|---|
| T(K) | 200 | 500 | 1000 |
| $T_2, T_3$ | 0.47 | 0.47 | 0.47 |
| $\sigma_{\mathit{eff}1}$ (×10⁻¹⁸ m²) | 4.4 | 2.6 | 1.8 |
| $\sigma_{\mathit{eff}2}$ (×10⁻¹⁸ m²) | 37 | 22 | 15 |

The expected photon count for each LIDAR system embodiment can subsequently be determined using algorithms, and subsequently correlated to radioactivity. The expected photon count, N(z), can be calculated as the sum of three terms:

$$N(z) = N_S(z) + N_b + N_D$$

where $N_S(z)$ represents the signal detected from the scatterers at range, z, $N_B$ represents the photon counts that are due to background skylight conditions, and $N_D$ represents the detector noise. These terms can be expressed as:

$$N_S(z) = \eta T_1 T_2 \left( \frac{E_1 R_L \Delta t}{\frac{hc}{\lambda_1}} \right) [\sigma_{\mathit{eff}1} \gamma_2 \rho(z) \Delta z] \frac{A_R}{4\pi z^2},$$

$$N_B = \eta [H_N R_L \Delta t \pi (\Delta \theta_R / 2)^2 A_R \Delta \lambda] \frac{(2\Delta z / c)}{(hc)/\lambda_2}, \text{ and}$$

$$N_D = (C_N R_L \Delta t)(2\Delta z / c)$$

where η is the receiver efficiency, $T_1$ is the atmospheric transmission at the transmission wavelength $\lambda_1$, $T_2$ is the atmospheric transmission at the detected wavelength $\lambda_2$, $E_1$ is the laser energy per pulse (Joules), $R_L$ is the repetition rate of the laser (S⁻¹), ρ(z) is the concentration of scatterers at range (z) (meters⁻³), $\sigma_{\mathit{eff}1}$ is the effective backscatter cross section at $\lambda_1$ (meters²), h is Planck's constant (~6.63×10⁻³⁴ J s), c is the speed of light (~3×10⁸ m/s), $A_R$ is the area of the telescope (meters²), $H_N$ is the background sky radiance (W/m² μm sr), $\Delta\theta_R$ is the field of view of the receiver (rad), Δλ is the bandwidth of the detector (micrometers), and $C_N$ is the dark count rate for the detector (seconds⁻¹).

The effective absorption cross section frequency, $\sigma_{\mathit{eff}}(\nu)$, for each LIDAR system can be determined by:

$$\sigma_{\mathit{eff}}(\nu) = \frac{\sigma}{(\Delta \nu_D^2 + \Delta \nu_L^2)} \exp\left[ -\frac{4\ln 2(\nu - \nu_1)^2}{\Delta \nu_D^2 + \Delta \nu_L^2} \right], \text{ where}$$

$$\sigma_0 = \frac{\sqrt{\ln 2}}{4\pi \sqrt{\pi}} A \left( \frac{c}{\nu_1} \right)^2 \frac{g_2}{g_1}, \text{ and}$$

A is the Einstein spontaneous emission coefficient (s⁻¹), and $g_1=(2J_1+1)$ and $g_2=(2J_2+1)$ are the degeneracies of the initial and the excited states, respectively $N_B$ and $N_D$ are constant with range, and the total expected noise signal ($N_B + N_D$) can be estimated from the photon count profile beyond the range of the scattering layers. Photon counting is a statistical process with a Poisson distribution, and the actual measurement has a variance equal to the expected value. Thus the signal-to-noise ratio (SNR) can be written as:

$$SNR = \frac{N_S}{\Delta N_S} = \frac{N_S}{(N_S + N_B + N_D)^{1/2}}$$

This statistical uncertainty determines the fundamental tradeoff between the resolution and the accuracy of the measurement. The measurement can be integrated over time and/or range (increasing Δt and/or Δz) to increase $N_S$ and to obtain the required accuracy at the expense of measurement resolution. The resolution and accuracy of the LIDAR measurements can be improved when the average laser power, $P_L(=E_1 R_L)$, and the telescope area ($A_R$) are increased.

Other embodiments of the present invention provide alternative methods of detecting radioactive materials at a distance. One alternative embodiment provides a method of detecting radioactive material by measuring escaping ionized air by moving the ionized air to a short range ion detector. The readings from the ion detector can be correlated to the estimated number of ions to which the detector is exposed.

Another alternative embodiment provides a method of detecting radioactive material using differential absorption (the "DIAL technique"). Because the ions absorb light from the laser beam when it is tuned to the correct wavelength, the amount of absorption is directly related to the concentration of ions. Two wavelengths are transmitted: one "on-line" wavelength that is absorbed by the molecular species of interest and one "off-line" wavelength that is unaffected by that species. The differential absorption magnitude between the two wavelengths is related to the concentration of the species. The absorption line can have a strength (absorption per molecule) of approximately 10⁻²⁴ to 10⁻²² centimeters (cm) and a lower state energy less than 300 cm⁻¹. In addition, the differential optical thickness between the on-line and off-line wavelengths can be between 0.03 and 0.1. The DIAL technique has a particular advantage in that: it is self-calibrating. Factors involving system parameters that may change over time such as filter transmissions, mirror reflectivities, and detector gains cancel in the DIAL data analysis equation.

Numerous characteristics and advantages have been set forth in the foregoing description, together with details of structure and function. While the invention has been disclosed in several forms, it will be apparent to those skilled in the art that many modifications, additions, and deletions, especially in matters of composition characteristics, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

What is claimed is:

1. A method of indirectly detecting a radioactive source by measuring ionization proximate the radioactive source, comprising:

transmitting pulsed light into an unenclosed air cloud proximate the radioactive source;

inducing non-fluorescing ions proximate the radioactive source to become fluorescing ions with the pulsed light;

filtering backscattered light emitted from the unenclosed air cloud the radioactive source to produce filtered backscattered light, wherein the filtered backscattered light includes only photons emitted from the fluorescing ions; and receiving the filtered backscattered light.

2. The method of claim 1, wherein the receiving the filtered backscattered light further comprises measuring an intensity of the filtered backscattered light by detecting at least a portion of the number of photons emitted from the fluorescing ions in the backscattered light.

3. The method of claim 2, further comprising correlating the intensity of the filtered backscattered light to a corresponding radioactivity measurement.

4. The method of claim 1, wherein at least a portion of the fluorescing and non-fluorescing ions are nitrogen ions.

5. The method of claim 1, wherein at least a portion of the fluorescing and non-fluorescing ions are oxygen ions.

6. The method of claim 1, wherein at least a portion of the fluorescing and non-fluorescing ions are argon ions.

7. The method of claim 1, wherein at least a portion of the fluorescing and non-fluorescing ions are helium ions.

8. The method of claim 1, wherein the transmitted pulsed light comprises a transmitted light of a wavelength that causes the non-fluorescing ions to fluoresce.

9. A method of indirectly detecting a radioactive source at a distance by measuring ionization proximate to the radioactive source, comprising:
    transmitting pulsed light into a volume surrounding the radioactive source, wherein the volume comprises both fluorescing and non-fluorescing ions, and wherein the volume is in an open environment;
    inducing the non-fluorescing ions with the pulsed light to become fluorescing ions;
    filtering backscattered light emitted from the volume surrounding the radioactive source to produce filtered backscattered light, wherein the filtered backscattered light includes only photons emitted from the fluorescing ions; and
    receiving the filtered backscattered light.

10. The method of claim 9, wherein the receiving the filtered backscattered light further comprises measuring an intensity of the filtered backscattered light by detecting at least a portion of the number of photons emitted from the fluorescing ions in the backscattered light.

11. The method of claim 10, further comprising correlating the intensity of the filtered backscattered light to a corresponding radioactivity measurement.

12. The method of claim 9, wherein the fluorescing and non-fluorescing ions are nitrogen ions.

13. The method of claim 9, wherein the fluorescing and non-fluorescing ions are oxygen ions.

14. The method of claim 9, wherein the fluorescing and non-fluorescing ions are argon ions.

15. The method of claim 9, wherein the fluorescing and non-fluorescing ions are helium ions.

16. The method of claim 9, wherein the transmitted pulsed light comprises a transmitted light of a wavelength that causes the non-fluorescing ions to fluoresce.

17. A method of indirectly detecting a radioactive source at a distance by measuring ionization proximate to the radioactive source, comprising:
    transmitting a first pulsed light into an unenclosed air cloud, the first pulsed light having a first wavelength into a volume surrounding the radioactive source, wherein the volume comprises both fluorescing and non-fluorescing ions, and wherein the first wavelength is absorbed by a molecular species of interest;
    transmitting a second pulsed light into an unenclosed air cloud, the second pulsed light having a second wavelength into the volume surrounding the radioactive source, wherein the second wavelength is unaffected by the molecular species of interest; and
    measuring a differential absorption magnitude between the first and second wavelength.

* * * * *